United States Patent [19]

Schnell et al.

[11] 3,996,027
[45] Dec. 7, 1976

[54] SWIRLING FLOW BUBBLE TRAP

[75] Inventors: William J. Schnell, Arlington Heights; Ludwig Wolf, Jr., Barrington, both of Ill.

[73] Assignee: Baxter Laboratories, Inc., Deerfield, Ill.

[22] Filed: Oct. 31, 1974

[21] Appl. No.: 519,731

[52] U.S. Cl. .................................. 55/36; 55/41; 55/52; 55/205; 210/512 R
[51] Int. Cl.² .................................. B01D 19/00
[58] Field of Search .................. 55/36, 41, 52, 159, 55/191, 204, 205, 460; 210/22, 321, 512

[56] References Cited
UNITED STATES PATENTS

| | | | |
|---|---|---|---|
| 1,440,808 | 1/1923 | Wineman | 55/205 |
| 2,434,596 | 1/1948 | Spieth | 55/205 X |
| 2,762,451 | 9/1956 | McNeil | 55/204 |
| 3,014,553 | 12/1961 | Jerman et al. | 55/205 |
| 3,753,336 | 8/1973 | Drew et al. | 210/512 R |
| 3,771,290 | 11/1973 | Stethem | 55/205 |

*Primary Examiner*—Charles N. Hart
*Assistant Examiner*—Richard W. Burks
*Attorney, Agent, or Firm*—Paul C. Flattery; Garrettson Ellis

[57] ABSTRACT

A device for separating low density materials such as gas bubbles from a liquid is disclosed which comprises a chamber defined by an inner wall which in turn defines generally circular, transverse cross-sections about a longitudinal axis. The liquid inlet port extends through the inner wall in a position to pass liquid into the chambers circumferentially about the inner wall for swirling flow within the chamber. Accordingly, lower density components of the fluid, such as bubbles, migrate away from the inner wall toward the center of the swirling flow. An outlet port extends through the inner wall, and is spaced from the inlet port, to collect fluid which is free from the low density materials.

2 Claims, 4 Drawing Figures

U.S. Patent     Dec. 7, 1976     3,996,027
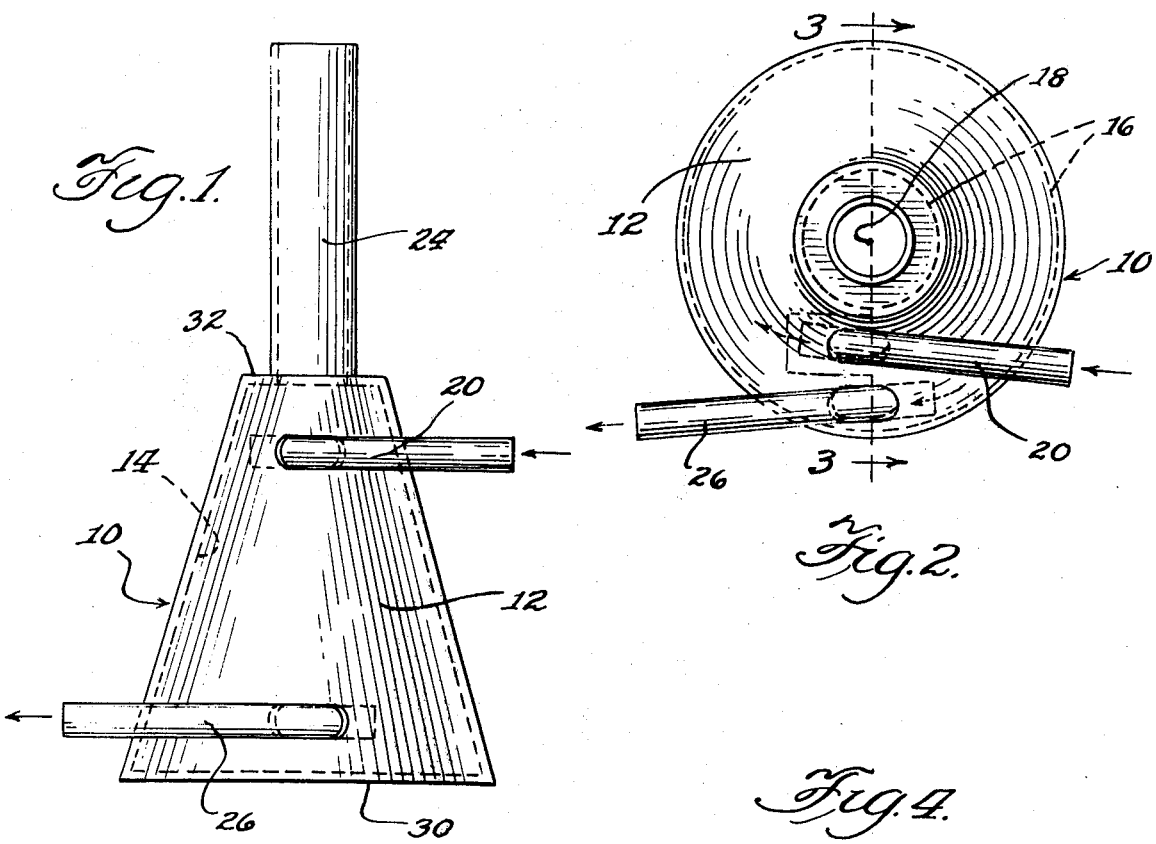
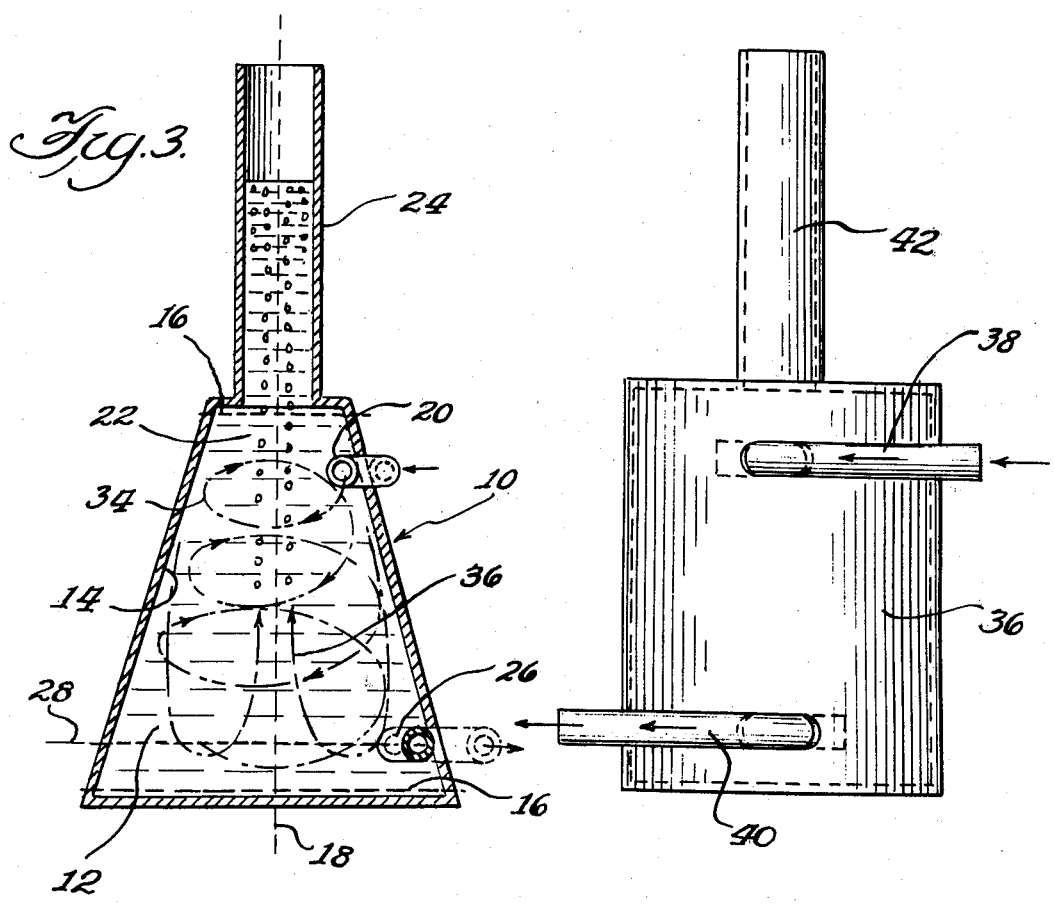

SWIRLING FLOW BUBBLE TRAP

BACKGROUND OF THE INVENTION

There are various different kinds of bubble traps for removing gas bubbles or other low density components from flowing liquid streams. In the medical field, it is very critical to remove all gas bubbles from blood which has been extracorporeally treated, and is being returned to the patient, for example in blood dialysis or blood oxygenation. Similarly, flowing streams of solutions, e.g. extracorporeal blood dialysis solution, or parenteral solutions such as peritoneal dialysis solution, are most desirably separated from any bubbles which may have been formed through heating, depressurization, or the like.

In the prior art, difficulties have been encountered in removing all of the bubbles from flowing liquid streams, particularly from liquid streams which have a relatively high volume of flow, as may be found in a typical extracorporeal blood dialysis processes. There is also a need for a reliable bubble removing device which is inexpensive, and which operates without the use of moving parts, so that it maintains functional reliability over a long period of time.

In accordance with this invention, a simple device for removing gas bubbles and other low density components from streams of blood, medical solutions, or any other desired liquid is disclosed. The device of this invention removes bubbles from relatively large-volume, swiftly flowing streams of liquid without the use of moving parts, and with great simplicity of construction.

DESCRIPTION OF THE INVENTION

The device of this invention comprises a chamber defined by an inner wall, which in turn defines generally circular transverse cross-sections about a longitudinal axis. A liquid inlet port passes through the wall and is positioned to pass liquid into the chamber circumferentially about the inner wall, to permit fluid passing through the inlet port to flow in circumferential manner about the inner wall, thus creating a swirling centrifugal flow within the chamber. As a result of this, lower density components of the fluid migrate away from the inner wall toward the center of the swirling flow. An outlet port passes through the inner wall in a position spaced from the inlet port, to collect fluid which is free from bubbles or other low density materials.

Typically, a collection port which is positioned adjacent the upper end of the longitudinal axis of the device, in position of use, is provided for removal of the bubbles or other low density materials as they spiral inwardly to the vicinity of the longitudinal axis, and rise out of the swirling liquid.

It is frequently preferable for the inner wall of the chamber to be generally conical in shape, having wider and narrower respective ends, and generally defining a truncated cone of the type shown in the drawings. The narrower end of the conical chamber preferably points upwardly in position of use.

The outlet port may also desirably extend in the direction of a tangent to an adjacent portion of the circumference of an adjacent, transverse cross-section of the chamber inner wall, but in a circular orientation opposite to that of the inlet port. As a result of this, the swirling liquid flows directly into the outlet port without excessive turbulence, and without undue disruption of the swirling flow in the chamber.

The inlet port is desirably positioned in the vicinity of the narrower end of the conical chamber, while the outlet port is positioned in the vicinity of the wider end of the chamber, so that the two ports are vertically spaced from each other in position of use. Accordingly, as fluid is forcefully passed into the chamber through the inlet port, it initially tends to swirl in the upper part of the chamber, tending to drive gas bubbles and the like inwardly as described above. As liquid is withdrawn from the outlet port from the bottom of the chamber adjacent the larger end thereof, the rapidly swirling liquid in the upper end of the chamber is brought downwardly in a spiral-like flow, which tends to further urge bubbles to the center of the device. At the same time, the conical shape of the chamber causes the swirling action to slow down at the larger, lower end of the chamber, for more desirable removal of the liquid through the outlet port.

In the drawings,

FIG. 1 is an elevational view of one embodiment of a bubble separating device made in accordance with this invention.

FIG. 2 is a plan view of the device of FIG. 1.

FIG. 3 is a sectional view taken along Line 3—3 of FIG. 2.

FIG. 4 is an elevational view of a modified bubble separating device made in accordance with this invention.

Referring to FIGS. 1, 2, and 3, bubble trap 10 is disclosed comprising a chamber 12 defined by inner wall 14. Inner wall 14 defines generally circular transverse cross-sections, such as at 16 in FIGS. 2 and 3, about a longitudinal axis 18.

Liquid inlet port 20 passes through wall 14 and is positioned to pass liquid into chamber 12 in circumferential manner about the inner wall, for swirling flow within the chamber. As a result of this, bubbles 22 or other lower density components (as schematically shown in FIG. 3) migrate away from inner wall 14 toward the center of the swirling flow which is generally about axis 18. Simultaneously, the bubbles rise and pass into bubble removal port 24 for venting or other removal.

Liquid outlet port 26 is preferably positioned near the bottom of the container in position of use, being vertically spaced from inlet port 20, and adjacent wall 14. Outlet port 26 is also spaced substantially from axis 18 so that bubbles 22 are driven away from wall 14 toward the vicinity of axis 18, and are not drawn into outlet 26. Outlet port 26, like inlet port 20, also extends in the direction of a tangent to an adjacent portion of the circumference of an adjacent transverse cross-section 28 of inner wall 14. However, outlet port 26 in a circular or circumferential orientation opposite to that of inlet port 20 (as indicated in FIGS. 1 and 2), so that outlet port 26 directly receives swirling liquid into it for efficient withdrawal of bubble-free fluid, without undue disruption of the swirling flow within chamber 12.

Chamber 12 and wall 14 are generally conical in shape, as shown in FIG. 1, with the chamber ends 30, 32 being respectively relatively wider and narrower. Narrower end 32 points upwardly in position of use. The result of this is, when used in accordance with this invention, that a highly desirable, complex flow pattern as illustrated in FIG. 3 is created, in which the spiral vortex flow pattern schematically illustrated at 34 is accompanied with a vertical vortex pattern 36. In this pattern, exterior portions of the spiralling fluid, adjacent wall 14, tend to flow slowly downwardly, while interior portions of the vortex, in the vicinity of axis 18, tend to flow upwardly, which serves to urge the gas bubbles in more complete and effective manner into bubble removal port 24.

Accordingly, fluid which enters inlet port 20 travels in a spiral pattern about wall 14 near the top of chamber 12. However, the outer portions of this spirally flowing liquid slowly move downwardly, while at the same time throwing bubbles 22 inwardly to the vicinity of axis 18 by centrifugal action, since the liquid components of the mixture are more dense than the gas bubbles, or any other light components that may be present.

Hence, liquid that has spiralled downwardly to outlet 26 can be bubble-free, and may be withdrawn for use in an artificial kidney or the like through outlet port 26.

Referring to FIG. 4, a cylindrical chamber 36 is provided having inlet port 38 and outlet port 40, which are positioned in circumferential relation to the inner wall to correspondingly expel and collect liquid, and to create a circumferential liquid flow within said cylindrical chamber 36. Accordingly, bubbles and other low density components are urged inwardly to the center of rotation, which is in line with collection port 42. The bubbles rise into port 42, from which they may be vented or otherwise removed.

Once again, the outlet is vertically spaced from the inlet, so that spiralling liquid which has reached the bottom of chamber 36 will be bubble-free.

The invention of this application provides a bubble trap or device for removing other relatively low density materials in large quantities and on a continuous flow basis without the use of moving parts. As such, it finds particular utility in the field of dialysis, but also in many other aspects of the processing of liquids for any desired purpose.

The above has been offered for illustrative purposes only, and is not intended to limit the scope of the invention, which is as defined in the claims below.

We claim:

1. In a method for separating low density materials such as gas bubbles from a liquid utilizing a chamber having an inner side wall defining generally circular, transverse cross sections about its longitudinal axis, said inner wall being generally conical in shape with a lower, wider end and a narrow, upper end, the interior of said chamber being free of flow-restricting baffles, the steps comprising: inserting said bubble-containing liquid into said chamber adjacent said upper end in a direction to pass liquid into said chamber circumferentially about the inner side wall for swirling flow within said chamber, and withdrawing said liquid in a tangential direction from said chamber adjacent the lower end thereof, while simultaneously withdrawing any gas bubbles present from a port positioned adjacent the upper end of the longitudinal axis of said chamber, while keeping said chamber essentially full of liquid, whereby said liquid flows in a spiral vortex flow pattern, in which exterior portions of spirally flowing liquid adjacent said side wall flow downwardly, while interior portions of said spirally flowing liquid, adjacent said longitudinal axis, flow upwardly to facilitate the removal of gas bubbles.

2. The method of claim 1, utilized in conjunction with the delivery of dialysis solution to an artificial kidney.

* * * * *